United States Patent [19]

Bucalo

[11] 4,257,427
[45] Mar. 24, 1981

[54] METHOD FOR COLLECTING BODY FLUIDS

[76] Inventor: Louis Bucalo, 155 Roberts St., Holbrook, N.Y. 11741

[21] Appl. No.: 75,249

[22] Filed: Sep. 13, 1979

Related U.S. Application Data

[60] Division of Ser. No. 746,827, Dec. 2, 1976, Pat. No. 4,186,730, which is a continuation-in-part of Ser. No. 534,893, Dec. 20, 1974, Pat. No. 3,998,211, which is a continuation-in-part of Ser. No. 499,925, Aug. 23, 1974, Pat. No. 3,934,575, and Ser. No. 499,926, Aug. 23, 1974, Pat. No. 3,924,607, each is a division of Ser. No. 329,862, Feb. 5, 1973, Pat. No. 3,842,166.

[51] Int. Cl.³ .............................................. A61B 10/00
[52] U.S. Cl. ..................................... 128/769; 435/294
[58] Field of Search ............... 128/1 R, 769, 759, 260, 128/285, 286, 294, 295, 760, DIG. 24; 435/294

[56] References Cited

U.S. PATENT DOCUMENTS

| 3,057,344 | 10/1962 | Abella et al. | 128/769 |
|---|---|---|---|
| 3,118,439 | 1/1964 | Derrenoud | 128/769 |
| 3,308,039 | 3/1967 | Nelson | 128/759 |
| 3,312,221 | 4/1967 | Overment | 128/DIG. 24 X |
| 3,315,660 | 4/1967 | Abella | 128/769 |
| 3,485,235 | 12/1969 | Felson | 128/769 |
| 3,688,763 | 9/1972 | Cromarty | 128/769 X |
| 3,844,285 | 10/1974 | Laby | 128/260 |
| 3,906,935 | 9/1975 | Raia et al. | 128/762 |

Primary Examiner—Kyle L. Howell
Attorney, Agent, or Firm—Steinberg & Raskin

[57] ABSTRACT

A method for collecting fluids present at the body of a human being or animal. An enclosure is temporarily situated at a cavity of the body, this enclosure having within itself a hollow interior for receiving a body fluid while shielding the body from the interior of the enclosure and while a part of the enclosure is situated at the body cavity in proximity to a location where a body fluid which is to be collected is situated. The enclosure carries a transfer structure which creates between the interior of the enclosure and the above location of the body fluid conditions for only inward transfer of the body fluid from this latter location into the interior of the enclosure, the inward transfer conditions being maintained effective during at least part of the time while the enclosure remains at the body cavity. Thereafter, when the enclosure is separated from the body cavity, the desired body fluid will be situated in the interior of the enclosure.

1 Claim, 15 Drawing Figures

METHOD FOR COLLECTING BODY FLUIDS

CROSS REFERENCE TO RELATED APPLICATION

This application is a division of application Ser. No. 746,827, filed Dec. 2, 1976, now U.S. Pat. No. 4,186,730 which in turn is a continuation in part of application Ser. No. 534,893, filed December 20, 1974 now U.S. Pat. No. 3,988,211, which in turn is a continuation in part of Ser. No. 499,925 filed Aug. 23, 1974, now U.S. Pat. No. 3,934,575 and Ser. No. 499,926, filed Aug. 23, 1974, now U.S. Pat. No. 3,924,607, which latter two applications are divisions of Ser. No. 329,862 filed Feb. 5, 1973, now U.S. Pat. No. 3,842,166, said last mentioned application basically teaching the introduction into a body cavity of a device which collects fluid from the cavity while therein and retaining the fluid after removal from the cavity so that the collected fluid can be analyzed, tested, or the like.

BACKGROUND OF THE INVENTION

The present invention relates to a method for collecting body fluids.

Thus, the present invention relates to a method for collecting at a body cavity of a human being or animal body fluids which may contain certain microorganisms, so that in this way it is possible to determine the presence of certain microorganisms.

At the present time when the presence of a given microorganism is suspected at a given part of the body of an individual, in order to determine whether or not in fact such a microorganism is present, it is conventional to transfer a body fluid which is suspected of carrying the microorganism to a suitable growth medium where the microorganism, if in fact it is present, will grow so that by inspection of the growth medium the presence or absence of the microorganism can be determined. For such purposes it is conventional to apply a swab to a part of the body where the presence of a given microorganism is suspected, this swab removing part of the body fluid such as mucous or the like which is suspected of carrying the microorganism, and then the swab is placed in contact with a suitable nutrient for transferring the body fluid with the suspected microorganism therein to the nutrient medium. Thereafter the nutrient is placed, for example, in a suitable incubator for a given period of time in an atmosphere which is favorable for growth of the microorganism, and after elapse of this period of time, the growth medium is inspected to determine whether or not in fact the suspected microorganisms have grown and are therefore present in the body.

Procedures and devices of the above type have inherent disadvantages. Thus, there is a considerable inconvenience in requiring a physician or other skilled individual to extract from the body of an individual materials which are suspected of containing a given microorganism and then transferring the extracted material to a growth medium which must then be placed in an atmosphere suitable for growth. In addition to the inconvenience of these procedures, a considerable amount of equipment is required, and very often physicians will mail swabs with specimens thereon to laboratories for testing. Thus, under these latter conditions a considerable delay is involved as well as a considerable risk that the microorganisms, if they are present, will die during the interval between removal from the body and contact with a nutrient at a laboratory, for example, after transportation time has elapsed.

Also, certain microorganisms cannot remain alive when subjected even to a slight temperature change upon leaving the body.

Moreover, completely aside from the above factors, the conditions under which microorganisms are artificially grown cannot fail to be different from the conditions which obtain in the body where the microorganism may be located. Because of these different growing conditions, it is possible to arrive at inaccurate results according to which unnecessary treatments will be given to an individual or according to which necessary treatments will not be given.

SUMMARY OF THE INVENTION

It is accordingly a primary object of the present invention to provide a method which will avoid the above drawbacks.

Thus, it is an object of the present invention to provide a method according to which it is possible to collect body fluids which, for example, may have certain microorganisms present therein, with the body fluid being collected directly at a body cavity where the body fluid is present and in such a way that the body is shielded from the collected body fluid, with the latter being prevented from returning to the body.

Also, it is an object of the present invention to provide a method according to which an agent is present in an enclosure to give the collected body fluid a given condition. For example if microorganisms are present in the body fluid, the agent may be antibiotic or a nutrient which will provide for a given condition of the body fluid directly within the enclosure without any possible influence on the body.

Thus, it is an object of the present invention to provide a method of the above type which will create no particular discomfort and which will in no way result in deterioration of the health condition of a given individual or animal.

It is also an object of the present invention to provide a method of the above type which are exceedingly simple and convenient to use.

Also it is an object of the present invention to provide a method according to which it becomes possible to grow cultures in a relatively simple and inexpensive manner while at the same time maintaining fully hygienic conditions.

It is furthermore an object of the present invention to provide a method of the above type which lend themselves to determination of the presence of a large variety of microorganisms in a manner which will give a clear indication of the presence or absence of the microorganisms.

According to the method of the invention for collecting fluids present at the body of a human being or animal, there is situated at a cavity of the body an enclosure which has within itself a hollow interior for receiving a body fluid while shielding the body from the interior of the enclosure and while situating a part of the enclosure at the body cavity in proximity to a location where a body fluid which is to be collected is situated. Between the interior of the enclosure and the location of the body fluid at the exterior of the enclosure there are created conditions for only inward transfer of the body fluid into the interior of the enclosure, and these conditions are maintained effective at least part of the time while the enclosure remains at the body cavity, so that thereafter when the enclosure is separated from the body cavity the desired body fluid will be situated in the interior of the enclosure.

The device includes an enclosure means for occupying a position at the body cavity with one part of the enclosure means situated adjacent a location where the body fluid to be collected is present, and this enclosure means of the invention is enclosed at least to an extent sufficient to prevent escape of fluid from the interior to the exterior of the enclosure means. A transfer means is situated at the one part of the enclosure means which is situated adjacent the body fluid for transferring the latter from the exterior to the interior of the enclosure means.

BRIEF DESCRIPTION OF DRAWINGS

The invention is illustrated by way of example in the accompanying drawings which form part of this application and in which.

DESCRIPTION OF PREFERRED EMBODIMENTS

Figures 1, 2, 3:
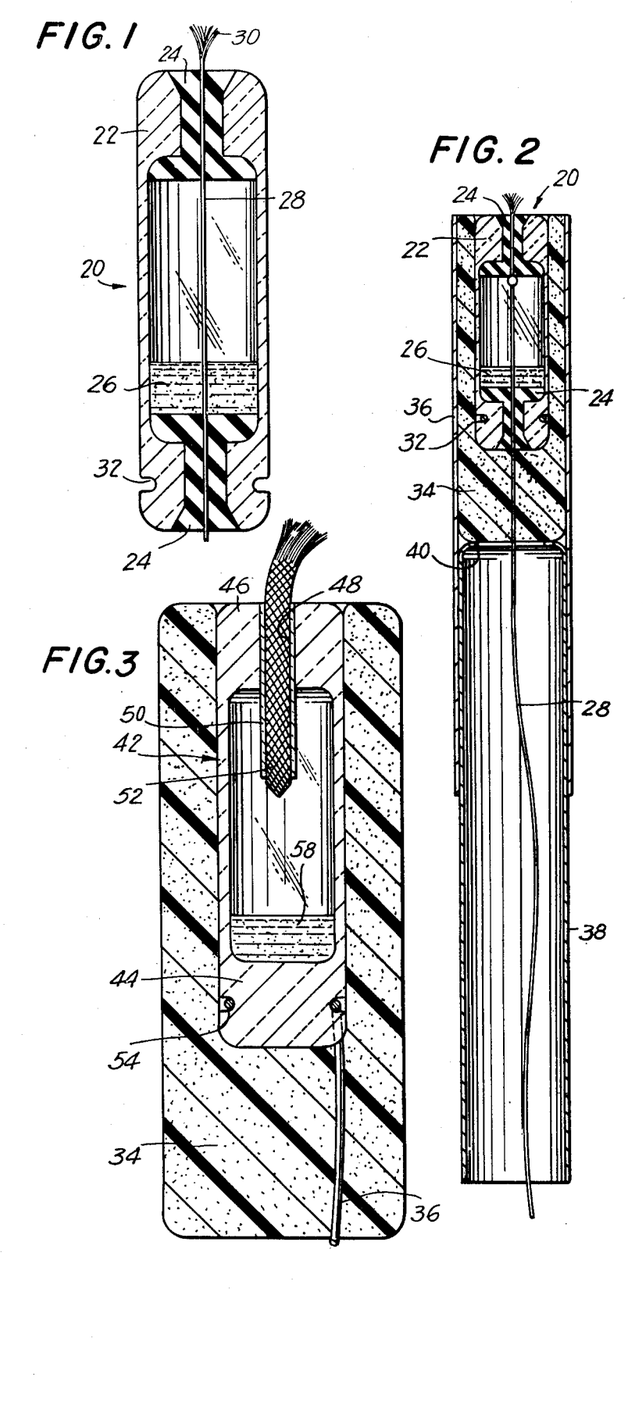
FIG. 1 is a sectional elevation of one embodiment of a structure of the invention for carrying out the method of the invention.
FIG. 2 is a longitudinal sectional elevation of a structure for supporting the device of FIG. 1 and for introducing the same into a body cavity.
FIG. 3 is a sectional elevation of another embodiment of a device of the invention.

Referring first to FIG. 1, there is illustrated therein an enclosure means 20 in the form of an elongated container 22 made of a suitable clear, transparent plastic such as polyethylene which may be relatively soft so that it has a certain amount of flexibility, although this latter property is not essential with the embodiment of FIG. 1. The opposed ends of the elongated enclosure means 20 are provided with a pair of opposed closure plug means 24 which close openings formed in the plastic container 22, in the manner illustrated in FIG. 1. These plugs 24 may be made of a material such as rubber or any other suitable plastic. Thus it will be seen that the enclosure means 20 is completely closed. However, before this enclosure means 20 is completely closed an agent such as a nutrient means 26 is situated therein. This nutrient means 26 may be in the form of a suitable broth which can be in its entirety in the form of a liquid although it can also be absorbed in a suitable medium such as cotton fibers and can have any desired viscosity. The composition of the nutrient means 26 is well known in connection with growth of cultures, this nutrient means 26 being capable of growing a culture from microorganisms which are placed in contact with the nutrient means 26.

In accordance with the method of the invention the enclosure means 20 is introduced into a body cavity in such a way that the upper part of the enclosure, as viewed in FIG. 1, is situated at a body cavity in close proximity to a location where there is a body fluid in which, for example, it is suspected that certain microorganisms are present. With the method of the invention after this enclosure and nutrient therein are situated in the above manner in the body cavity, conditions are created for transferring a body fluid from the location where the presence thereof is encountered into the interior of the enclosure means into engagement with the nutrient means therein. These conditions are created in the embodiment of FIG. 1 by way of an elongated filament or string 28 which passes completely through the plugs 24 while frictionally engaging the same. Thus it will be seen that while the filament or string 28 passes through the closure plugs 24 nevertheless the interior of the enclosure 22 remains closed. At the upper part of the enclosure 20 which is situtated in the vicinity of the body fluid, the string 28 carries a means 30 for receiving a body fluid if indeed it is present at the location where the upper end of the enclosure of FIG. 1 is situated. This means can take the form of a suitable wick or other absorbent medium connected to the outer end of the filament 28 which is shown at the top of FIG. 1. For this purpose it is only necessary to abraid the filament 28 so as to fray the outer end portion thereof situated above the enclosure means 20, as viewed in FIG. 1, and in this way a part of the filament itself forms the means 30 for receiving the body fluid if it is present. Thus this means 30 will engage mucous or the like which may contain the suspected microorganism, so that in this way the microorganism is received by the means 30.

With this structure of the invention which is shown in FIG. 1, after it is situated in the selected location, according to the method of the invention, the monofilament 28 is pulled downwardly as viewed in FIG. 1, so that the receiving means 30 with the microorganism received thereby is pulled through the upper closure plug 24 into the interior of the container 22. Once this means 30 moves through the upper plug 24 it will simply fall to the nutrient means 26 to place any microorganism in the means 30 in contact with the nutrient means. The operator can feel the reduction in the force required to pull the string 28 as soon as the means 30 moves into the interior of the enclosure beyond the upper closure plug 24, so that the operator will then know that no further pulling of the string 28 is required. If desired, however, the string 28 can be pulled completely through the lower plug 24 also so that the operator can completely remove the string 28 if so desired.

It is to be noted that the container 22 is provided at the region of its lower end with an exterior groove 32 capable of receiving one end region of a string which can be fastened at the groove 32 to the enclosure 22 so that through such a string it is possible in any event to separate the enclosure from the body cavity.

This structure is permitted to remain in the body cavity for a length of time sufficient for the culture to grow, and thereafter it is removed and the culture medium can be inspected directly through the clear plastic material to determine the presence of certain microorganisms. Also, through one or both of the plugs 24 the nutrient means 26 is accessible for application of suitable staining mediums, for example, which can aid in recognizing certain mircoorganisms.

Referring now to FIG. 2, it will be seen that the entire device 20 of FIG. 1 is situated within a cup-shaped body 34 of a soft material such as a suitable foam polyethylene, for example. Both the cup-shaped body 34 as well as the container 22 are of a circular cross section, and the cup-shaped body 34 has a top open end, as viewed in FIG. 2, where the top end of the container 22 is exposed so that the portion 30 of the filament 28 will also be exposed. The cup-shaped body 34 is introduced into the body cavity with the device 22 seated in the cup-shaped body in the manner illustrated in FIG. 2, so that by way of the soft cup-shaped body 34 there will be no discomfort to the individual.

In order to be able conveniently to introduce the device of the invention into a body cavity, the cup-shaped body 34 is situated in the interior of an elongated outer tube 36 made of any suitable relatively rigid cardboard, plastic, or the like. Telescoped within the outer tube 36 is a pusher 38 which may be in the form of a tube having at its upper end, as viewed in FIG. 2, an inwardly directed flange 40 which will engage the bottom end of the body 34 in the manner illustrated in FIG. 2.

Thus, with this construction it is possible very conveniently to introduce the structure of the invention into a body cavity. For example if the portion 30 of the filament 28 is to be situated in engagement with the cervix, then the telescoped elements 36 and 38 are operated in the manner of conventional elements of this type used to introduce a cylindrical type of tampon into the vagina during the menstrual period. Thus, the upper end of the tube 36, as viewed in FIG. 2, will be initially introduced into the vagina, and then the pusher 38 will be advanced to displace the cup-shaped body 34 out of the tube 36 and along the interior of the vagina until a resistance is felt indicating that the upper end of the container 22 and the part 30 of the filament 28 are situated next to the cervix. With the cup-shaped body 34 thus held in this way at the desired location, the operator will pull on the string 28 which it will be noted extends completely through and beyond the tube 38. Thus, any body fluid such as mucosa or the like situated at the cervix and carrying possible microorganisms such as those of ghonorrea, for example, or any vaginitis microorganisms, will become situated in the portion 30 together with mucosa or the like absorbed thereby, and such microorganisms if they are present will be pulled together with the string 28 through the upper plus portion 24 while the container remains closed. The pulling of the string in the above manner is delayed, however, until the container has been in the body for a time sufficient for the entire assembly to assume the temperature of the body. As was indicated above once the portion 30 of the string 28 moves inwardly beyond the plug 24 shown at the top end of the container 22 in FIG. 1, the operator will feel reduction in the resistance to pulling on the filament 28, and thus it will be known that the portion 30 has reached the interior of the container 22 and can fall freely into engagement with the nutrient 26. If desired, however, the operator can continue to pull on the string 28 so as to remove the latter completely through the lower plug 24 also. In either case, once the part 30 has engaged the nutrient 26 the tube 38 can be removed while the cup-shaped body 34 together with the device 20 remains in the body so that microorganisms, if they are present, can grow in the nutrient means 26 while the latter together with the container 22 remains in the body.

After a given length of time it is possible to remove the body 34 together with the device 20 from the body cavity. For this purpose a suitable string may be attached to the groove 32 or if the string 28 remains it can be used for this purpose.

It is to be noted that with the above-described method and structure of the present invention it is possible to grow cultures from suspected microorganisms directly in the body cavity where the presence of the microorganisms is suspected so as to closely simulate for the growth of the culture the conditions which are present in the body cavity itself. In addition, because the container 22 is completely closed there is no possibility of providing in the body itself conditions which will enhance the growth of the microorganisms in a manner which will cause greater deterioration to the body itself from the growth of the microorganisms. Thus with the method and structure of the invention the body is safely shielded from any possible ill effects resulting from growing the microorganisms in the body itself.

As was indicated above, once the cup 34 is removed it is a simple matter to remove the device 22 and then carry out whatever steps are required to determine whether or not a culture growth in the nutrient 26 contains the suspected microorganisms.

A further variation of the structure of the invention is shown in FIG. 3.

According to this embodiment the device 42 is in the form of a container similar to the container 22 made of the same material. However in this case the device 42 has a closed bottom end 44, as viewed in FIG. 3, while the upper end 46 is formed with an elongated opening 48 which is of a relatively small diameter. This opening 48 is lined with an elongated plastic or glass tube 50 which has compressed in its interior a wick 52, as illustrated in FIG. 3. This wick 52 has an upper free end portion which projects beyond the upper end of the container 42 in the manner shown in FIG. 3. Moreover the entire container is seated in a cup-shaped body 34 which is identical with that of FIG. 2. However it will be noted that in FIG. 3 the groove 54 which corresponds to the groove 32 of FIG. 1 has a string 56 situated therein and extending through and beyond the soft cup-shaped body 34 in the manner illustrated.

Figure 4:
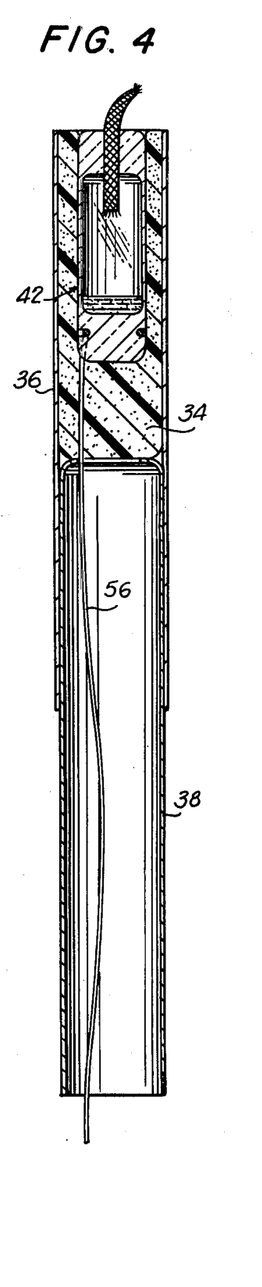
FIG. 4 is a sectional elevation showing structures similar to that of FIG. 2 for introducing the device of FIG. 3 into a body cavity.

This structure which is shown in FIG. 3 is seated in an outer tube 36 in the manner shown in FIG. 4 with a pusher 38 being provided as was the case with FIG. 2. Thus the embodiment of FIG. 3 can be introduced into a body cavity in the same way the embodiment of FIG. 1. In this case, however, the cup-shaped body 34 together with the device 42 is simply placed in the body cavity with the upper free end of the wick at the upper part of the container 42 being situated at the region where the presence of certain microorganisms is suspected. After the length of time required for growth of a suitable culture the entire device 42 together with the body 34 are removed by pulling on the string 56.

It is to be noted that the embodiment of FIG. 3 will operate in a particular manner. Thus, the wick 52 by being compressed within the tube 50 which in turn has a sealed engagement at its outer surface in the opening of the part 46 of container 42 serves to substantially close the container while at the same time permitting by the absorbent action of the wick a body fluid with suspected microorganisms therein to pass through the wick into the interior of the container 42 where the nutrient 58 is situated. This body fluid with suspected microorganisms therein will form at the lower interior end of the wick, as viewed in FIG. 3, a drop which will separate itself from and fall from the wick to the nutrient medium 58. As successive droplets of body fluid with suspected microorganisms therein fall from the wick the level of the nutrient medium, which may be a liquid broth, for example, will arise toward the wick thus reducing the interior space above the liquid material in the interior of the container 42. In this way the pressure of the latter space will increase to limit the extent to which the dripping of the body fluid into the interior of the container 42 can take place. The plastic or glass tube 50 prevents any liquid which may be situated in the interior of the container beside the wick from engaging the latter. At the same time, because of the increased pressure in the space above the liquid in the container 42 the dripping will stop because an equilibrium will be reached when the pressure becomes great enough to prevent any further fluid from entering through the wick, and thus in this case also there is provided a container capable of growing a culture in its interior without in any way contaminating the body in which the device of the invention is situated.

As was the case with FIG. 1, the device of FIG. 3 is removed after a given time and then suitable procedures can be carried out with respect to the nutrient to determine whether or not any culture which grows therein contains suspected microorganisms.

Figure 5:
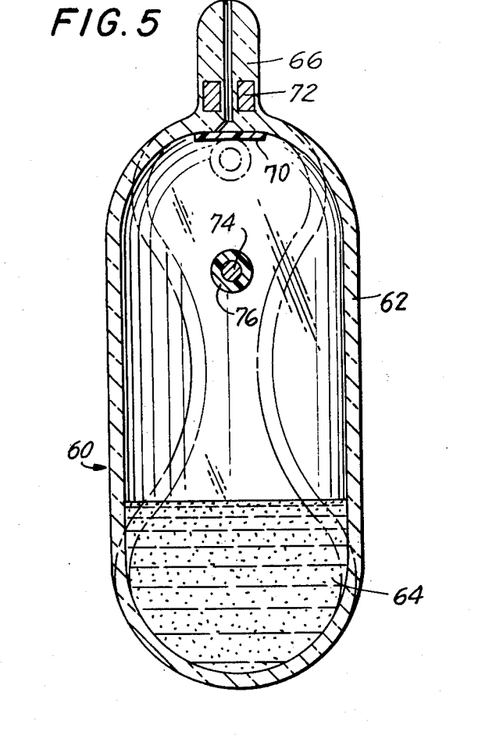
FIG. 5 is a schematic sectional elevation of a further embodiment of a device of the invention shown in phantom lines in a compressed condition.

Referring now to FIG. 5, there is illustrated therein a device 60 according to the present invention, this device being capable of being introduced into a body cavity by way of an outer tube and an inner pusher as was the case with the embodiments of FIGS. 1 and 3. However, in this case the device 60 is made of a flexible clear plastic material such as a suitable relatively soft polyethylene. In this way the device 60 is provided with a container 62 which is flexible as well as being resilient to a substantial extent.

In its lower end region the container 62 encloses a nutrient means 64 which may be in the form of a broth having suitable nutrients therein, and this nutrient medium may be contained in a suitable absorbent filamentary structure if desired. As was the case with the embodiments of FIGS. 1 and 3, the nutrient medium may also have in it antibiotics for preventing the growth of microorganisms in which there is no interest and the presence of which may render identification of suspected microorganisms more difficult to carry out.

The upper part of the container 62 of FIG. 5, which forms the upper part thereof when it is introduced into a body cavity, is formed with a relatively short neck 66 having a narrow bore 68 of small diameter passing therethrough. At its inner surface, the container 62 carries a flap valve 70 which is capable of opening to permit fluid to enter the interior of the container 62 but which closes if fluid tends to flow out of the container 62. This flap valve 70 is thus in the form of a simple leaf of plastic material joined at one edge in a suitable way to the inner surface of the container 62. It is to be noted that the container 62 as well as the containers of FIGS. 1 and 3 and those described below may originally be in the form of a pair of half shells which are joined together at a suitable seam or they may be split initially between their opposed ends and then joined circumferentially, so that it is a simple matter to introduce into these containers the desired materials before the containers assume the configuration disclosed in the drawings.

When the neck portion 66 of the container 62 is formed as by molding in an injection mold, for example, this part of the container is molded around a magnetic body 72 made of any suitable magnetic alloy, for example, and having the configuration of a ring or the configuration of a pair of opposed relatively small magnetic bodies. The body or bodies 72 are initially provided in a known way with a fairly substantial magnetic force. Moreover, there is situated in the interior of the container a small spherical body 74 also made of a magnetic material and additionally provided with a substantial magnetic force, the polarity of the body 74 having with respect to the polarity of the body or bodies 72 a relationship according to which the body 74 is attracted toward the body 72. In order to prevent contamination of the nutrient 64 by the metallic material of the body 74, it is embedded in a covering of inert plastic material 76.

Initially the above-described structure is held with the flap valve 70 displaced to a position opening the bore 68, for example by inserting through the bore 68 a rod of extremely small diameter holding the flap valve 70 in at least a slightly open position in opposition to the magnetic force tending to close the flap valve by the attraction between the body 74 and the magnetic means 72. With the parts held in this position the interior of the container 62 is evacuated in any suitable way so that the container is in a compressed condition of restricted volume as shown in dotted lines in FIG. 5. Thus the evacuation of the interior of the container 62 will cause the outer atmosphere to compress the container 62 so that it will assume the dotted line configuration illustrated in FIG. 5, and when the container 62 has been compressed to the desired extent in this manner the small pin which holds the flap valve 70 in its slightly open position is withdrawn so that the flap valve 70 now closes and the magnetic valve means serves to maintain the flap valve in its closed position so that initially the parts have the condition shown in dotted lines in FIG. 5.

It is in this condition that the structure is introduced into a body cavity in the manner described above in connection with FIGS. 1-4, and of course when the embodiment of FIG. 5 is introduced into the body cavity the neck 66 is placed at its outer free end in engagement with the part of the body where it is suspected that certain microorganisms are present.

With the device 60 of FIG. 5 thus situated in the desired location, the bodies 72 and 74 are demagnetized in a well known manner, simply by situating a suitable electrical field at the exterior of the body of the individual in the region of the magnetic bodies 72 and 74. This reduction in the magnetic force will permit the flap valve 70 to open while the walls of the container 62 expand to the solid line condition illustrated in FIG. 5, with the result that a certain quantity of body fluid which may have suspected microorganisms therein is drawn through the bore 68 into the interior of the container 62. Thus the container 62 will assume a solid line position shown in FIG. 5 and a certain quantity of body fluid with suspected microorganisms therein will be situated in the interior of the container in engagement with the nutrient 64. Of course, any tendency of fluid to flow out of the container will be prevented by the flap wire 70, so that an effective means is provided to prevent a reversal of the flow thus localizing all growth of microorganisms to the interior of the container without any possible danger to the individual.

In this case also after a predetermined length of time the container 62 will be removed and the nutrient medium will be inspected to check on the presence or absence of suspected microorganisms.

Of course the device 60 of FIG. 5 may be situated in a suitable cup-shaped supporting body as described above in connection with FIGS. 2 and 4, and a suitable string may be attached to the container of FIG. 5 to facilitate withdrawal thereof from the body cavity.

Figure 6:
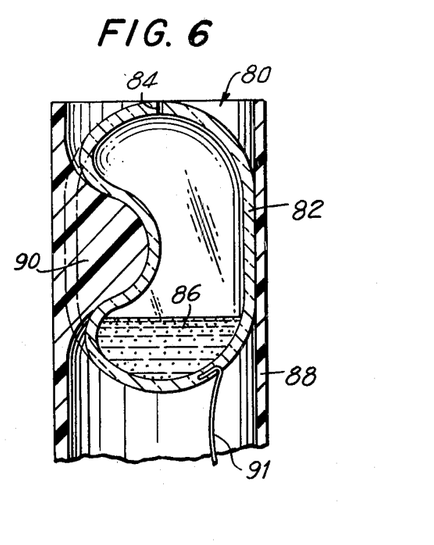
FIGS. 6–8 are respectively schematic sectional elevations of various possible embodiments of the invention with means for initially holding the enclosures in a compressed condition of restricted interior volume.

Referring now to FIG. 6, the embodiment of the invention illustrated therein also includes a device 80 having a flexible resilient container 82 made of a clear plastic as was the case with FIG. 5. However, in the case of FIG. 6 the container 80 is only provided at its upper end, which becomes situated uppermost when situated at the body, with a slit or with a minute pinhole type of opening 84. A nutrient means 86, corresponding to any of the nutrient means referred to above, is situated in the container 82 as illustrated.

According to this embodiment there is also an outer tube 88 through which the device 80 is pushed into the interior of the body cavity in the manner described above in connection with FIGS. 2 and 4. However, in this case the outer tube 88 is provided at its interior with a bulging portion 90 which serves to deform the container 82 in the manner illustrated in FIG. 6, so that in this way the container 82 has a restricted interior volume. The pusher which is used with the outer tube 80 differs from the pusher of FIGS. 2 and 4 in that this particular pusher will have a portion which is cut away so as to clear the bulging portion 90 while the pusher displaces the container 82 past the bulging portion 90. The result is that the container 82 is introduced into the body cavity in a compressed condition of restricted interior volume. As soon as the unit 82, however, moves beyond the bulging portion 90, it will expand slowly due to its inherent resiliency, drawing fluid in through the minute opening 84, and if any of this fluid has the suspected microorganisms they will of course contact the nutrient means 86. In this case also the container 82 has a suitable string attached thereto as, for example, a string 91 embedded in a wall of the container 82 and projecting from this wall so as to be accessible for withdrawing the container 82 after a given length of time sufficient for microorganisms to grow in the nutrient means 86 while the container 82 remains in the body cavity.

Of course, with this embodiment of FIG. 6 it is also possible to situate the container 82 in a cup-shaped body made of a soft material, as was the case with the embodiments of FIGS. 1-3, and in this event the bulging portion 90 would compress the soft cup-shaped body and act through the latter on the container 82 in order to compress the latter in the manner shown in FIG. 6.

Thus with this simple embodiment of FIG. 6 it is also possible to achieve an automatic expansion of the container 82 when its slit 84 becomes situated at the location where it is suspected that certain microorganisms are present, so that if indeed these microorganisms are present they will be sucked in through the slit 84 into the interior of the container 82 together with any body fluids which carry the microorganisms.

Figure 7:
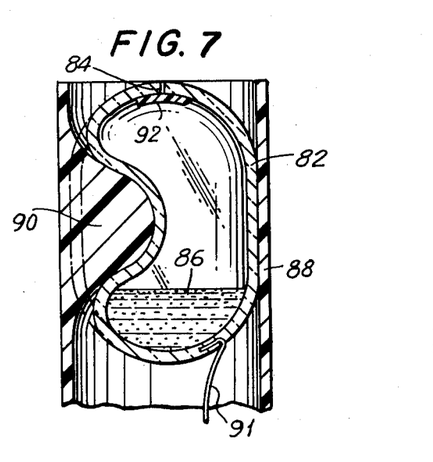

The embodiment of FIG. 7 is identical with that of FIG. 6, except for the fact that with the embodiment of FIG. 7 the container 82 is provided in its interior with a flap valve 92 which normally maintains the small minute opening 84 closed but which of course is capable of turning inwardly away from the opening 84, the flap valve 92 being fixed, for example, to the inner surface of the container 82 only at the right edge region of the flap valve 92, as viewed in FIG. 7. Thus, with this embodiment, all of the features described above in connection with FIG. 6 will be the same, the only difference being that the flap valve 92 automatically yields to permit fluid, with suspected microorganisms therein, to enter into the container 82, while the flap valve 92 will reliably prevent any fluid from escaping from the interior of the container 82. Thus with the embodiment of FIG. 7 it is possible to provide an opening 84 which is somewhat larger than the slit 84 of the embodiment of FIG. 6.

Figure 8:
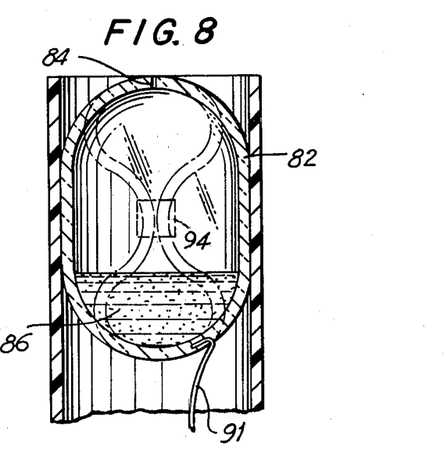

With the embodiment of the invention which is illustrated in FIG. 8, there is also a container 82 which is identical with the container 82 of FIG. 6. However, in this case, the container 82 is initially maintained in a compressed condition of restricted interior volume, as shown in dotted lines in FIG. 8, by way of a ring 94 which is made of a material which will dissolve in the interior of the body. Such materials are well known. Thus, with this embodiment before the container is introduced it is compressed to the dotted line condition and maintained in this compressed condition by the ring 94, and then the container 82 of FIG. 8 is introduced into the interior of the body cavity in the manner described above, so that the slit 84 becomes situated at the location where it is suspected that certain microorganisms are present.

After the container 82 of FIG. 8 remains at the cavity of the body for a given time, the conditions prevailing in the interior of the body cavity will cause the ring 94 to dissolve and thus release the container 82 so that by its own inherent resiliency it will expand back to its initial condition shown in solid lines in FIG. 8. The result is that during this expansion fluids in the body cavity with suspected microorganisms in these fluids are drawn into the interior of the container 82 of FIG. 8 so as to engage the nutrient means 86 therein.

Of course, with the embodiment of FIG. 8 it is also possible initially to locate the device 82 in a cup-shaped body of soft material as described above. However, it is to be emphasized that with the embodiments of FIGS. 6-8 as well as with those of FIGS. 1-3 it is not absolutely essential to provide the cup-shaped body with soft material. The devices of the invention are relatively small and normally will not create any particular discomfort even if they are introduced without the use of a cup-shaped body as described above. The latter may be used, however, in those cases where it is felt that a particular individual may be particularly sensitive.

Figures 9, 10, 11:
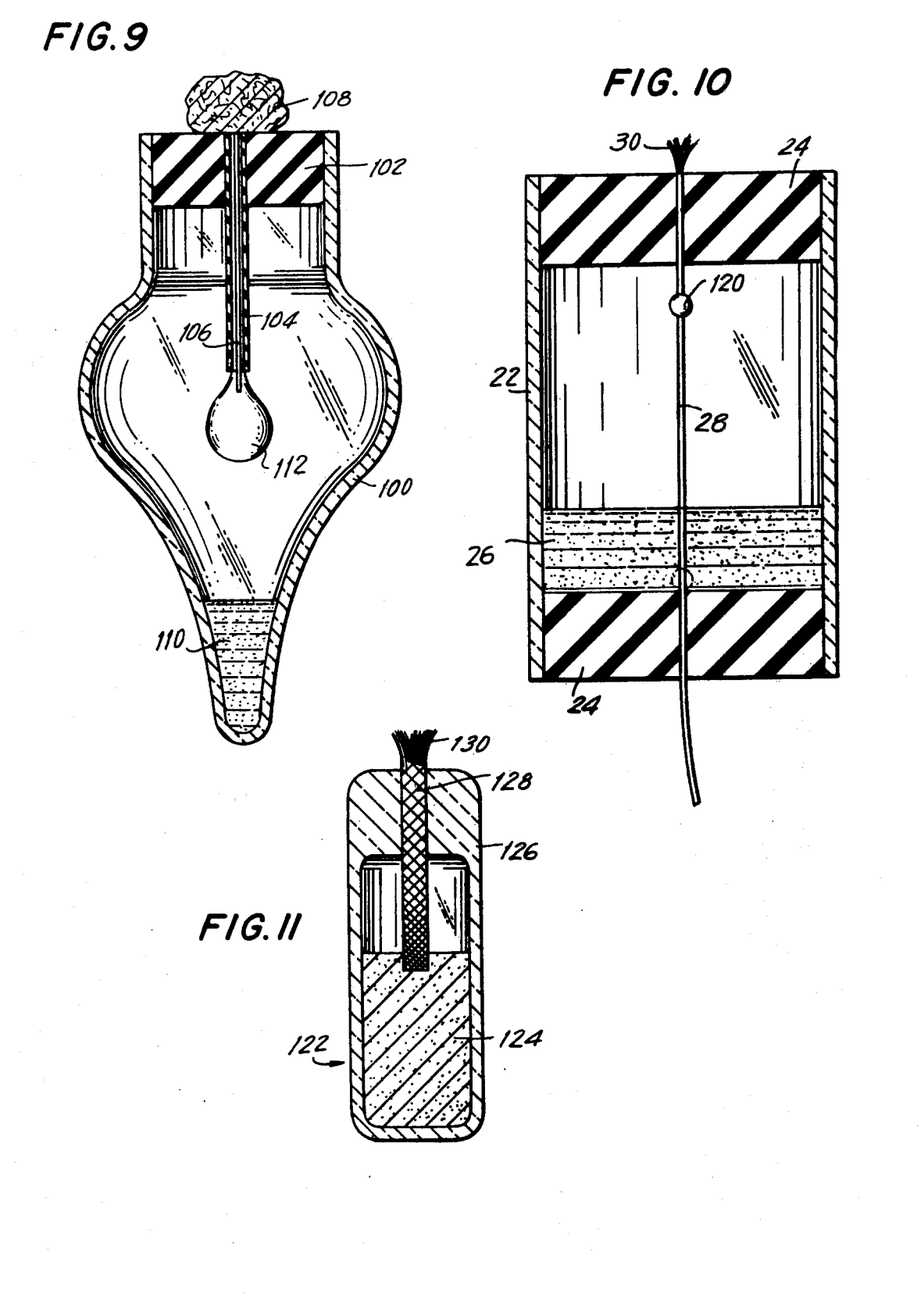
FIG. 9 is a schematic elevation of a structure of the invention which operates in a manner similar to that of FIG. 3.
FIG. 10 is a schematic elevation of a further variation of an embodiment of the invention as illustrated in FIG. 1.
FIG. 11 is a schematic elevation showing in section a further embodiment of the invention utilizing a dry nutrient.

The embodiment which is illustrated in FIG. 9 is essentially the same as the embodiment which is illustrated in FIG. 3. Thus, the embodiment of FIG. 9 has an outer container 100 which is made of a clear flexible resilient plastic material, this container being closed at its top end by a closure plug means 102 formed with an opening against the interior surface of which is located an elongated capillary tube 104 corresponding to the tube 50 of FIG. 3 except that the tube 104 is of a smaller diameter so as to have the capillary action which is desired for the embodiment of FIG. 9. With the embodiment of FIG. 9, instead of a wick, which extends through the interior of the tube, there is an outer relatively small body 108 of cotton or absorbent wadding, to engage that part of the body where it is suspected that certain microorganisms are present. A filamentary extension 106 of the wadding 108 extends downwardly through the interior of the capillary tube 104. A nutrient means 110 is situated in the interior of the container 100 at the lower region thereof.

It is to be noted that in this case the container 110 has the illustrated configuration according to which its largest diameter is at an intermediate portion surrounding the bottom end of the capillary tube 104 where a drop forms to fall from the bottom end of the capillary tube 104 to the nutrient means 110. This embodiment of FIG. 9 may also be situated in a suitable soft cup-shaped body to render greater comfort to the individual, and when it is introduced into the body, the cotton wadding 108 will engage the part of the body where it is suspected that certain microorganisms are present. The body fluid will then flow down the capillary tube to form a drop 112 as shown in phantom lines at the bottom of the capillary tube 104 in FIG. 9. Because of the larger diameter of the plastic container 100 at the elevation of the drop 112, there is sufficient space for this drop to form while the remainder of the container can be maintained at smaller dimensions, and at the same time as the level of liquid in the container builds, the pressure will increase, as was the case with the embodiment of FIG. 3, so as to limit the extent to which liquid will rise in the container. Thus, not only is a sufficient free space provided for the droplet in FIG. 9, but at the same time without increasing the amount of material used for the container 100 it is possible for a substantial amount of body fluid to enter so as to make certain that if any microorganisms which are suspected are indeed present they will be contained in the container 100 to grow as a result of the presence of the nutrient broth.

Of course, this embodiment of FIG. 9 also may be provided with a suitable string for withdrawing the device of FIG. 9 from the interior of the body.

The embodiment of the invention which is illustrated in FIG. 10 may be considered as being identical with that of FIG. 1 and is only illustrated schematically in FIG. 10 for the sake of simplicity. Thus it will be seen that there is schematically shown in FIG. 10 the container 22 having the opposed closure plugs 24 through which a monofilament or string 28 extends so that the upper roughened free end 30 of the string can receive a body fluid with suspecting microorganisms therein and be drawn into the interior of the container 22.

However, with the embodiment of FIG. 10 the string or monofilament 28 fixedly carries in the interior of the container 22 an inert bead 120 which limits the extent to which the string 28 will be pulled. Thus when the bead 120 reaches the phantom line position shown in FIG. 10 in engagement with the bottom closure means 24, the abraided part 30 of the string will surely have been introduced into the interior of the container below the upper closure plug 24, so that contact between a suspected microorganism and the nutrient medium 26 is assured while at the same time the extent to which the string 28 is pulled is limited by the inert bead 120 which is attached to the cord 28.

In all of the above-described embodiments there is situated within the container a nutrient medium which may be a suitable broth as referred to above. As a specific example, the nutrient medium may take the form of a Mueller Hinton Broth which may be present in an amount of, for example, 2.1 grams for each 100 ml total broth. With this latter broth there is contained in the total nutrient medium a certain amount of Agar which may be present in an amount of, for example, 0.150 grams for each 100 ml of broth. Of course, in addition to the above ingredients the remainder of the broth will be made up of water. It is possible to increase the amount of Agar for each 100 ml of total nutrient medium up to 0.200 grams where the nutrient medium will start to congeal at 37° C. Thus, by varying the amount of Agar in the nutrient means it is possible to control the viscosity thereof.

In addition, as was pointed out above, the nutrient means will contain certain antibiotics for the purpose of preventing growth of microorganisms in which there is no interest and the growth of which may serve only to confuse the indication of the growth of a particular microorganism in which there is an interest. Such antibiotics may be the following which are present in the indicated amounts:

| | | |
|---|---|---|
| Cholestimethate | 0.00563 | (5.6 mg) |
| Nystatin | 0.0090 | (9.0 mg) |
| Vancomycin | 0.0025 | (2.5 mg) |
| polymixin B | 0.00125 | (1.25 mg) |

Thus, antibiotics as set forth above may be included in the nutrient medium in the above amounts for each 100 ml of nutrient means.

The particular antibiotics referred to above will effectively kill *E. coli*, the growth of which might serve only to confuse the indication of the growth of other microorganisms.

In addition, in connection with the nutrient medium, it is to be noted that it is not essential that this nutrient medium be in the form of a liquid. As is apparent from the above description of the several embodiments of the invention, one of the primary advantages achieved by the present invention is that there can only be a flow of body fluid into the container but not out of the container, so that there can be no ill effects to a particular individual. This result of the present invention also can be achieved with an embodiment of the invention as illustrated in FIG. 11. Thus in FIG. 11 there is disclosed a container 122 which may also be made of a clear flexible plastic material through which the nutrient in the interior of the container is readily visible, as is the case with all of the above-described embodiments of the invention. However in this case the nutrient means 124 is initially dry. Thus a nutrient medium as set forth above may be absorbed by a suitable absorbent fibrous material which is packed into the container as illustrated in FIG. 11. However, when this nutrient means 124 is situated in the container 126 of the device 122, this nutrient is totally dry. In this case the upper end of the container which is to be situated in close proximity to the region where it is suspected that certain microorganisms are present is formed with an opening which is closed by a wick 128 having at its upper end a frayed portion 130 which will readily absorb body fluid with suspected microorganisms therein, and in this case the wick will serve to transfer the body fluid directly to the dry nutrient means 124. With this particular embodiment of the invention the amount of dry nutrient 124 situated in the container 126 is sufficient to require a relatively long time for the nutrient 124 to become completely saturated. With all of the embodiments of the invention the device may remain in the interior of the body for a period of time which is on the order of twelve hours. Thus with the embodiment of FIG. 11 a sufficient nutrient 124 is situated in dry condition in the container 126 so that a complete saturation of the nutrient 124 prior to elapse of a period on the order of twelve hours cannot take place. As a result during the entire time that the device of FIG. 11 remains in the body it is only possible for flow to take place toward the interior of the container but not toward the exterior thereof, with the result that there cannnot be any reverse flow out of the container of the invention, in the embodiment of FIG. 11, since the container of FIG. 11 will be separated from the body cavity prior to the time when the nutrient medium becomes totally saturated.

Thus, it will be seen that with embodiments of the invention as shown in FIGS. 1 and 10, the fact that the string or monofilament is frictionally pulled through the closure plugs will reliably prevent any reverse flow out of the container. In the same way, with the embodiments of FIGS. 3 and 9, the building up of the pressure within the container after fluid is delivered into the latter by the wick or capillary tube will prevent the fluid delivered to the interior of the container from flowing back out of the container. Thus in the case of FIG. 3 the fluid cannot have access to the wick because of the pressure which will build up in the interior of the container while in the case of FIG. 9 the same results are achieved, which is to say that the pressure in the interior of the container of FIG. 9 will become too great to enable the fluid delivered into the interior of the container to again have access to the filament 106 so as to be carried upwardly along the capillary tube back to the body. In this connection the embodiment of FIG. 9 is of particular significance inasmuch as the enlarged portion surrounding the area of the bottom end of the capillary tube 104 will prevent liquid in the container of FIG. 9 from engaging the bottom end of the capillary tube even if it should not be precisely vertical. The same of course holds true for the embodiment of FIG. 3 where the outer tube 50 will prevent any liquid from having access to the wick.

Of course, all of the above-described embodiments which have flap valves will be reliably prevented by such flap valves from affording the possibility of flow out of the container. Those embodiments which have simply a small minute opening such as a pinhole 84, as shown in FIGS. 6 and 8, are also particularly effective in this respect. Thus, it is to be emphasized that these openings 84 are normally completely closed. They are formed, for example, by a small slit which pass through the wall of the container. As a result of the presence of such a small slit, which need not have a length greater than 1/32 of an inch, for example, during the expansion of the container the edges which form the slit will yield inwardly to permit inward flow of fluid. However, once the containers reach their initial configuration these slits 84 become completely closed to prevent any possibility of flow of fluid out of the containers 82. It is to be noted in this connection that the inward flow of fluid takes place in all embodiments of the invention over a relatively long period of time which is on the order of several hours, for example from six to twelve hours. This result is achieved also by way of the slit 84 which permits the fluid to flow into the interior of the container only at an extremely low rate. Thus, with the embodiments of FIGS. 6 and 7, for example, when the containers 82 are deformed so as to push air out of the interiors of the containers, by the action of the bulges 90, these containers will not immediately resume their initial configuration. Because of the presence of the slit 84 it is not possible for air to be drawn rapidly back into the containers 82 and they remain in their compressed condition of restricted interior volume over a long period of time requiring several hours before the containers 82 resume their initial condition. The same effect of several hours of delivery of fluid at an extremely slow rate to the interior of the container is achieved with the other embodiments, with the possible exception of FIGS. 1 and 10 where the operator manipulates a string for this purpose. However it is to be emphasized that with these embodiments the operator will not manipulate the string to pull the suspected microorganism into the container until after the container has remained in the body cavity for a period of time sufficient to enable the entire device of the invention to assume, throughout all parts of the device of the invention, the temperature of the body in whose cavity the device is placed. Thus, it is known from experience that one of the most serious drawbacks of transferring microorganisms by way of a swab from the interior of a body to a suitable plate at the exterior of the body on which growth is to take place resides in the fact that the microorganisms are of necessity subjected to a change in temperature during such transfer operations. A temperature change which need only be on the order of 2° may be sufficient to kill certain microorganisms so that they will never grow and a test will be negative when in fact the microorganisms are present in the body. It is precisely such a drawback which is avoided with the present invention. Because the microorganism is drawn into the container of the invention over a long period of time, the device of the invention will be uniformly, throughout all of its parts, at the body temperature during travel of microorganism to the nutrient in the container of the invention. This factor, of course, shows the significance of the ring of FIG. 8. The ring 94 of FIG. 8 will only dissolve, as a result of the temperature of the body, after a given period of time whereby it is assured that the device of FIG. 8 will be at body temperature before any microorganisms reach the nutrient 86. However, the same advantages are achieved with the embodiments of FIGS. 1 and 10, as pointed out above, simply by delaying the pulling of the string until after the device has remained in the body for a sufficient length of time to assure a uniform body temperature throughout the entire device of the invention. Of course, those embodiments which have wick or capillary tubes will assure accurate indications of the presence or absence of certain microorganisms because they continue to deliver the fluid to the nutrient over a period of several hours.

The above-discussed important feature of the invention according to which a reverse flow of fluid out of the container back to the body is reliably avoided is carried out, in principle, even after the device is removed from the body. Thus it is equally important to prevent contamination of individuals who handle the device of the invention. Therefore, where inspection alone of the nutrient through the clear transparent wall of the container of the invention will not give the required information, it is possible to use certain dyes in order to bring out the presence or absence of suspected microorganisms with great clarity. Such dyes are readily introduced into the interior of the container of the invention without opening the container, so that the operator need never touch the nutrient medium within the container. For example one or more drops of a suitable dye can be introduced by way of a syringe the needle of which simply punctures through the wall of the container to enable the required amount of dye to be dropped onto the nutrient. In addition, where there are wicks, it is possible simply to apply the dye to a wick which will draw the dye into the container in order to spread the dye over the nutrient medium in order to give the required indication.

In connection with the nutrient means, as indicated above, it is not essential that this nutrient means be in the form of a liquid alone, since it can be absorbed in a suitable fibrous absorbent medium and can even be in a completely dry condition with the particular embodiment of the invention which is illustrated in FIG. 11 making special use of this latter type of nutrient.

It is to be noted that in some cases the collected body fluid itself will form a sufficient nutrient means, so that an additional nutrient means need not be provided.

Figure 12:
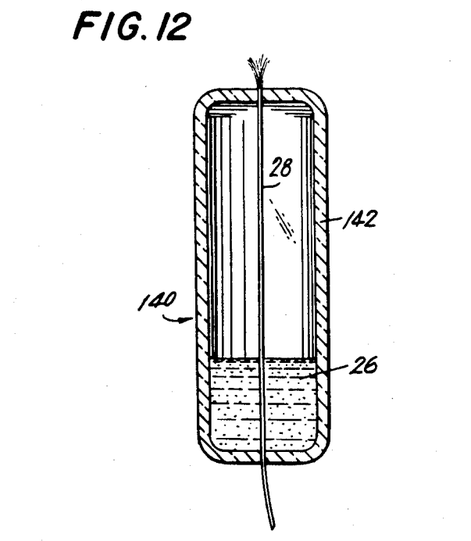
FIG. 12 is a sectional elevation of a further embodiment of the invention which is similar to the embodiment of FIG. 1.

Referring now to FIG. 12, there is illustrated therein an embodiment of the invention which is similar to that of FIG. 1. Thus FIG. 12 shows a device 140 constructed in accordance with the present invention for carrying out the method of the invention, this device 140 including a container 142 which is similar to the container 22 of FIG. 1 except that the container 142 does not have any plugs. The plastic material at the ends of the container 142 directly engage the filament or string 28 which may be identical with that of FIG. 1 and which is capable of being pulled in the same way into the container 142 so as to engage the nutrient 26 therein. When the container 142 is formed, the shells thereof, when joined together will directly engage the string 28 so that the latter is capable of being pulled through the ends of the container 142. Thus it is not essential to have plugs as shown in FIG. 1.

Figure 13:
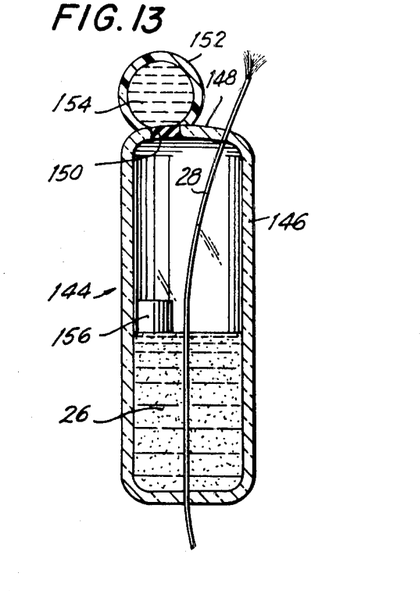
FIG. 13 shows a variation of the embodiment of FIG. 12 which is adapted to have a predetermined gaseous atmosphere generated.

Referring now to the embodiment of the invention which is illustrated in FIG. 13, it is desirable in connection with certain microorganisms to provide special atmospheres in which the microorganisms will have favorable growth conditions. For example certain microorganisms readily grow in a carbon dioxide atmosphere. With an arrangement as shown in FIG. 13 it is possbile to provide such an atmosphere. The device 144 of FIG. 13 includes a container 146 which may be identical with the container 142 of FIG. 12 and which has its end walls traversed by a string 28 in much the same way, as shown in FIG. 13. However, the top end 148 of the container 146 is formedwith an opening which is closed by a plug 150, and joined to the exterior surface of the top end 148 is a small flexible enclosure 152 made of a suitable plastic and containing a liquid 154, such as acetic acid. Situated directly on the nutrient 26 in the container 146 is a pellet 156 which may be a bicarbonate pellet. Just before the device of FIG. 13 is introduced into the body cavity, the flexible enclosure 152 is compressed so as to force the liquid 154 into the container 146 with the plug 150 yielding at this time as a result of the pressure applied to the container 152. When the acetic acid engages the pellet 156 there will be an automatic generation of carbon dioxide gas which fills the interior of the container 146 so as to provide an atmosphere which is highly favorable for the growth of cerain microorganisms.

Except for the above distinctions the embodiment of FIG. 13 operates in the same way the embodiment of FIG. 12.

Figure 14:
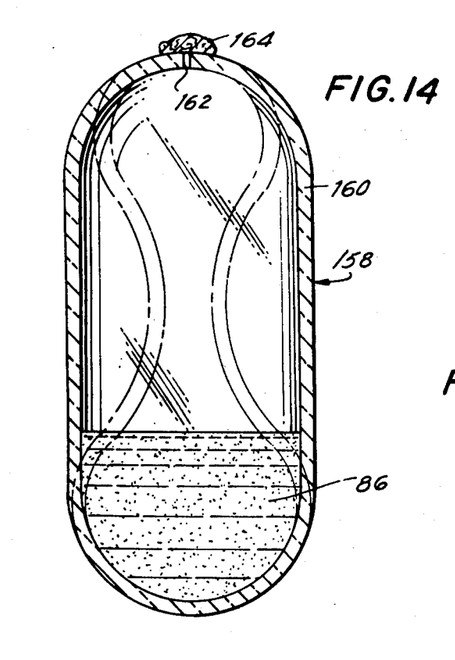
FIG. 14 shows a further variation of an embodiment similar to that of FIG. 8.

Referring now to FIG. 14, the device 158 of the invention which is illustrated therein includes a flexible clear transparent container 160 which may be identical with the container 82 shown in FIG. 8. This container 160 also has a slit 162 at its top end, and this slit is identical with the slit 84. However in this case of FIG. 14, when the container is compressed to assume the dot-dash line condition, instead of providing a ring 94 of dissolvable material around the central portion of the container, as shown in FIG. 8, a simple small body 164 is placed over the slit 162 in the manner shown in FIG. 14. This body 164 is made of a material which may be the same as the material of the ring 94. It will adhere to the exterior surface of the container 160 and will reliably close the slit 162 so that the container 160 will remain in its condition of restricted volume shown in dot-dash lines in FIG. 14 as long as the body 164 which can dissolve in the interior of the cavity remains in the position shown in FIG. 14. With this embodiment, the compressed container is introduced into the cavity with the slit 162 of course situated adjacent the region where it is suspected that certain microorganisms are present which should grow in the nutrient medium 86. Due to the temperature prevailing in the interior of the body cavity, the closure element 164 will dissolve and as soon as it disappears the slit 162 will become uncovered so that the container 160 can then gradually expand while drawing through the slit 162 body fluids with suspected microorganisms therein to grow, if they are present, in the medium 86, as described above in connnection with FIG. 8. Thus the embodiment of FIG. 14 will achieve the same results as the embodiment of FIG. 8 without requiring a ring 94 as is the case with FIG. 8.

Of course, the embodiment of FIG. 14 may be provided with a removal string similar to the string 91 of FIG. 8, and the same is true of the embodiments of FIGS. 12 and 13.

Figure 15:
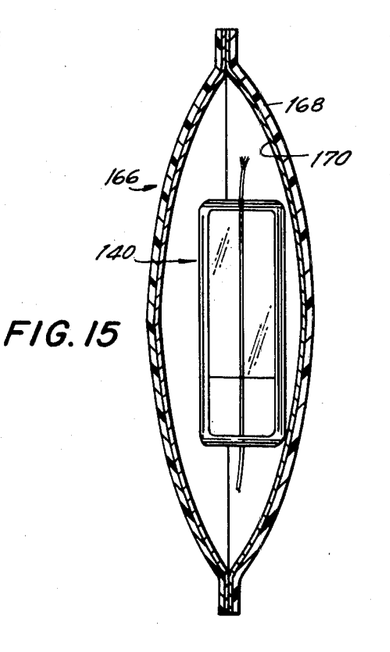
FIG. 15 illustrates the manner in which any of the embodiments of the invention can be packaged.

Any of the above-described embodiments of the invention may be packaged in such a way that they will have a long shelf life prior to use thereof. Thus, FIG. 15 shows a suitable package for the device 140 of FIG. 12, but it will be understood that this package can readily be used for any of the above-described devices of the invention. Thus, FIG. 15 shows a package 166 which has an outer layer 168 of a plastic such as polyethylene, this outer layer 168 being lined by an inner layer 170 of a suitable metal film such as an aluminum foil, for example. The device 140, or any of the other devices of the invention, is situated in the package prior to sealing thereof as shown in FIG. 15. Also, the sealing of the package takes place in an atmosphere which contains an inert gas which will serve to maintain the desired shelf life of the device which is packaged. For example the sealing of the package of FIG. 15 may take place in a carbon dioxide atmosphere, or if desired a nitrogen atmosphere may be used, so that the interior of the package contains a gas which will act to preserve the device of the invention over a long period of time, with the lined package acting to prevent undesirable migration through the wall of the package in the manner which would undesirably shorten the shelf life of the structure of the invention.

Although the devices of the invention may be made in various sizes and shapes, as a particular example, the total lengths of any of the above containers may be on the order of 1 inch while its diameter is on the order of 0.3 inches. The cup shaped body 34 will have a total length on the order of 1.5 inches and an outer diameter of approximately ½ inch, when used in the vagina.

What is claimed is:

1. In a method for collecting fluids from the body of a human being or animal, the steps of positionally arranging an enclosure in juxtaposition to a cavity of the body which at least at times contains body fluid in such manner that when the body fluid is present in the cavity the enclosure is in contact with the body fluid, said enclosure having within itself a hollow interior for receiving the body fluid while shielding the body from the interior of the enclosure, enclosing within the enclosure an agent which includes at least as a part thereof a nutrient for promoting the growth of certain microorgansims which may be present in the collected body fluid, creating between the interior of the enclosure and the body fluid conditions for transfer of the microorganism to the nutrient comprising a string which initially has a portion exposed at said part of said enclosure to receive said microorganism if it is present at said location, said string extending through a closed wall portion of said enclosure and being capable of being pulled though said closed wall portion at least to an extent sufficient for placing said portion of said string in engagement with the nutrient subsequent to introduction of the enclosure into the body cavity with said portion of said string situated at said location, and pulling said string through said closed wall portion to effect transfer of said microorganism, if it is present, into said enclosure, so that thereafter when the enclosure is separated from the body cavity, the microorganisms, if present in the body fluid, will be situated in the interior of the enclosure.

* * * * *